United States Patent [19]

Hetz

[11] Patent Number: 4,530,362

[45] Date of Patent: Jul. 23, 1985

[54] ULTRASOUND DEVICE FOR SECTOR SCANNING

[75] Inventor: Walter Hetz, Erlangen, Fed. Rep. of Germany

[73] Assignee: Siemens Aktiengesellschaft, Berlin and Munich, Fed. Rep. of Germany

[21] Appl. No.: 512,251

[22] Filed: Jul. 11, 1983

[30] Foreign Application Priority Data

Jul. 19, 1982 [DE] Fed. Rep. of Germany ....... 3226916

[51] Int. Cl.[3] .............................................. A61B 10/00

[52] U.S. Cl. ...................................... 128/660; 73/628; 73/633

[58] Field of Search .................. 128/660, 661; 73/780, 73/628, 641, 633, 634; 310/36, 156, 216; 336/217

[56] References Cited

U.S. PATENT DOCUMENTS

| | | | |
|---|---|---|---|
| 4,030,347 | 6/1977 | Norris et al. | 73/780 |
| 4,241,324 | 12/1980 | Douglass et al. | 336/217 |
| 4,264,162 | 4/1981 | Suzuki et al. | 354/436 |
| 4,287,767 | 9/1981 | Kretz | 128/660 |
| 4,315,435 | 2/1982 | Proudian | 73/628 |
| 4,326,786 | 4/1982 | Uchiyama et al. | 354/235.1 |
| 4,374,525 | 2/1983 | Baba | 73/633 |
| 4,424,503 | 1/1984 | Kashima | 336/217 |
| 4,433,691 | 2/1984 | Bickman | 128/660 |

FOREIGN PATENT DOCUMENTS

| | | |
|---|---|---|
| 2941865 | 5/1981 | Fed. Rep. of Germany . |
| 2945586 | 5/1981 | Fed. Rep. of Germany . |

*Primary Examiner*—Kyle L. Howell
*Assistant Examiner*—Ruth Smith
*Attorney, Agent, or Firm*—Mark H. Jay

[57] ABSTRACT

An ultrasound device for sector scanning which includes an ultrasound transmitting/receiving system. The system is housed in a compact cylindrical applicator housing which contains ultrasound transducer heads and associated ultrasound transducer elements at both ends of the applicator housing. Each of the two ultrasound transducer heads is rotatable within the applicator housing for performing sector scanning. A single drive mechanism rotates or swivels reciprocally both transducer heads so that undesirable inertial forces are cancelled or compensated. A guiding element pivotally supports the applicator housing so that the housing can be rotated and one or the other of the two ultrasound transducer heads be used. The guiding element also provides the enclosure for the electronics associated with the ultrasound applicator.

10 Claims, 4 Drawing Figures

ULTRASOUND DEVICE FOR SECTOR SCANNING

BACKGROUND OF THE INVENTION

The invention relates to an ultrasound device for sector scanning, which includes an applicator housing for an ultrasound transmission/receiving system and drive and control means. The ultrasound transmission/receiving system consists of an ultrasound transducer head with at least one transducer element. Additionally, the ultrasound transducer head can be swivelled around a swivel axis during specific time intervals to cover a predeterminable angle area.

The sector scan procedure is applied primarily for cardiac examinations. In actual use, ultrasound waves are transmitted and received through the acoustic window located between the ribs (intercostal) and above the collar bone (suprasternal) of a patient. Although many sector scanners are known, technological trends are moving toward the development of compact, and easily operable applicators.

Sector scans can be generated through mechanical or electronic methods. With respect to the mechanical method, an ultrasound transducer head is mechanically swivelled at a given periodic rate. In an electronic method, beam deflection operating according to the "phased array" principle is applied to generate scan areas. Furthermore, mechanically operated ultrasound transducer heads can be tilted by means of an eccentric with an associated push rod mechanism. In yet another mechanical embodiment, the ultrasound transducer head can be designed as a rotary shaft which carries several peripherally arranged, individual transducer elements, where the individual transducer elements are enabled or disabled in successive, cyclic intervals during shaft rotation. Finally, in a third alternative, an electro-magnetic drive mechanism may be used, which operates according to the principles of moving coil three-phase current, ac motors. Accordingly with the last mentioned drive method, controllable forces are generated via electro-dynamic fields, which influence the rotatable ultrasound transducer head.

As already mentioned, the developmental trend in the field of of ultrasound scanners is directed toward the creation of small and easily operable applicators. However, technical solutions applied in prior art applicators include adverse effects such as forces of inertia which occur within the applicator during mechanical operations of the ultrasound transducer head. Efforts have been made to compensate for these forces of inertia with clockwise and counterclockwise operating motors. However, prior art solutions remain unsatisfactory insofar as each ultrasound transducer head is operated with a specific ultrasound frequency. Generally the entire applicator has to be exchanged in order to be able to use different frequencies.

SUMMARY OF THE INVENTION

It is the object of the present invention to provide an ultrasound device which is mechanically simple and easy to operate and which incorporates many additional application oriented features.

According to the invention, this objective has been met by means of a single drive mechanism operating two ultrasound transducer heads which are introduced into one applicator housing and which are positioned opposite one another. The ultrasound transducer heads include respective transducer elements which are arranged to face in opposite direction to one another. The above single drive implementation produces the effect that during a scan motion which uses one ultrasound transducer head the other transducer head performs a swivel motion in opposite direction to stabilize the device and compensate for undesirable mechanical forces.

Therefore, the present invention includes both an advantageous solution which compensates for unavoidable inertial forces occurring within mechanically operated sector scanners, and a device which includes two ultrasound transducer heads operating with different operating frequencies. These transducer heads can be easily brought into a desired application position. In the present invention, the applicator with the two transducer heads is pivotally supported by a guiding element. The applicator can be longitudinally aligned with the guiding element and held in a pen like manner or its longitudinal axis may be offset with respect to the longitudinal axis of the guiding element as required for certain medical examinations. The ultrasound device of the present invention can be moved in all directions and is therefore very useful for cardiac examinations. The new design of the applicator housing with the guiding element provides superior useability and application versatility during examination of the intercostal or suprasternal cavity due to the guiding element.

Preferably, an electro-magnetic drive mode is used to realize the two different design modes of the mobile system. Mechanical complexity and resultant costs are reduced by using a double armature drive motor with respective coils and magnetic elements arranged thereon thus providing a small-sized applicator.

Other features and advantages of the present invention will be apparent from the following description of the preferred embodiments, and from the claims.

For a full understanding of the present invention, reference should now be made to the following detailed description of the preferred embodiments of the invention and to the accompanying drawings.

DETAILED DESCRIPTION

Figures 1, 4:
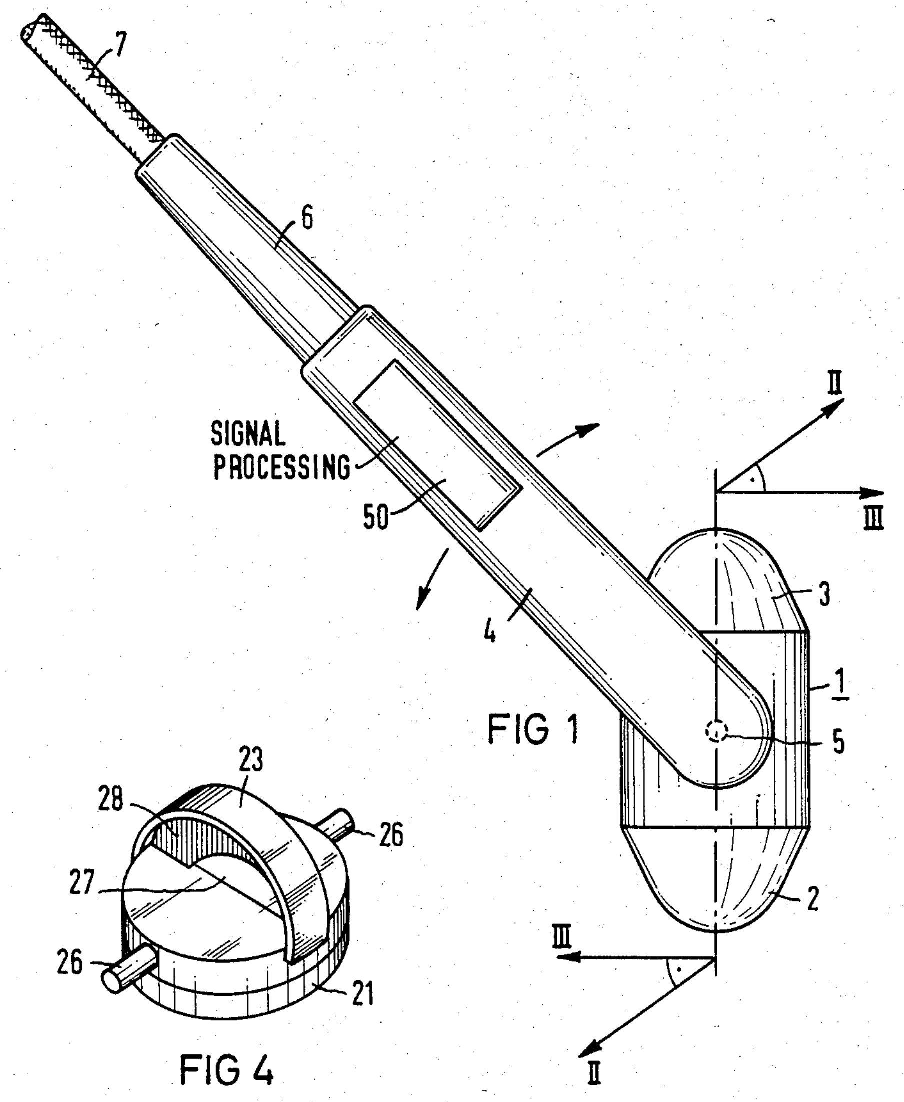
FIG. 1 illustrates a side-view of the device according to the invention.
FIG. 4 shows a perspective view of an ultrasound transducer head.

In FIG. 1, the applicator housing has been identified with 1. Applicator housing 1 is of a cylinder-type design and includes on its top and bottom two caps 2 and 3, shaped as approximately symmetrical spherical calotte halves. These calotte halve caps are comprised of flexible, but stable synthetics such as polyethylene or polypropylene. Each cap encloses one scanner together with the scanner's respective coupling fluid passage. Applicator housing 1 with scanner caps 2 and 3 is of extremely compact design. As a result, the applicator can be positioned between the ribs of a patient. Subsequently, sector scans for slice images of the heart can be generated.

At its center, applicator housing 1 is pivotally supported by guiding element 4. A connection for applicator housing 1 with axis of rotation 5 is arranged proximally on guiding element 4. Cable connection 6 with operating cable 7 is located distally (at the distal end) on guiding element 4. By means of the pivotal connection between guiding element 4 and applicator housing 1, it is possible to apply either one of the ultrasound transducer heads in a pen-like fashion for an intercostal examination or use them for a suprasternal examination by offsetting the longitudinal axis of the applicator from the corresponding axis of the guiding element.

Figure 2:
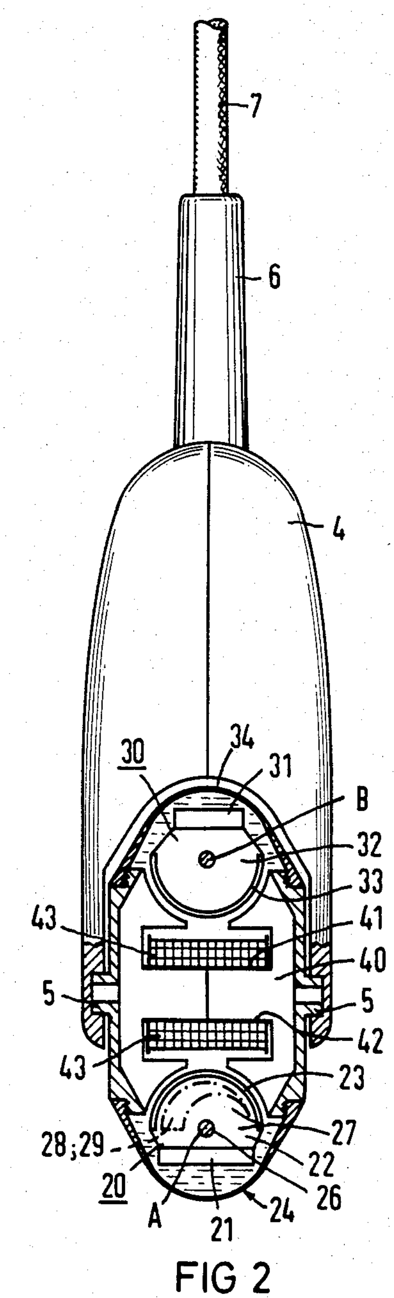
FIGS. 2 and 3 are views of FIG. 1 taken along directions II and III respectively.
Figure 3:
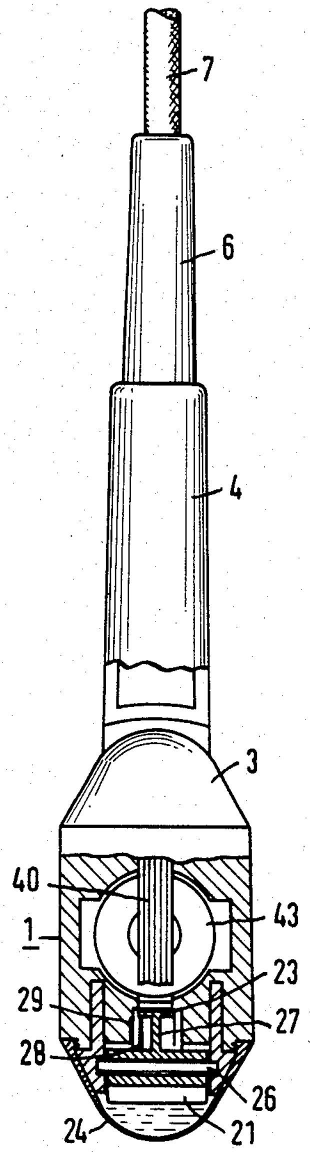

In the cross-sections illustrated in FIGS. 2 and 3, numbers 1-7 have been used for the same identification purposes as above. Applicator housing 1 is comprised in the main of synthetic material and includes an electromagnetic drive with yoke, coil and swiveling armature. By means of a bearing configuration arranged on each side of the housing of guiding element 4, applicator housing 1 is attached in a swivelling and/or tilting mode, so that either scanner can be brought into a suitable application position.

Two ultrasound transducer heads 20 and 30 are positioned in applicator housing 1 and can be rotated at a predeterminable angle around axis of rotations A and B respectively. In addition, ultrasound transducer elements 21 and 31 are arranged via attenuation layers (not shown) in the direction of application on ultrasound transducer heads 20 and 30 respectively. Ultrasound transducer heads 20 and 30 form swiveling armatures 22 and 32, which include permanent magnet layers 23 and 33 on their backsides. Such permanent magnets are formed, for example, from rare earths and are to be arranged layer-like onto armature parts 22 and 32. They are magnetized according to requirements, for example in circumferential succession of approximately 90° with a north pole, south pole and again a north pole. In the direction of application, ultrasound transducer heads 20 and 30 are enclosed by the previously mentioned caps 2 and 3. Essentially, the caps are part of the coupling system together with membranes 24 and 34, and an ultrasound-transmitting liquid, such as water. The ultrasound-transmitting liquid is located in the passages between the transducer elements and the membranes.

An electro-magnet is arranged between the rotatable ultrasound transducer heads 20 and 30, which simultaneously activates the motion of both ultrasound transducer heads. As such, the electro-magnet consists of layered transformer stampings 40, which have been punched out accordingly to provide pole shoes on the end side for the armature surfaces formed by the ultrasound transducer heads. In this manner a yoke with recesses 41 and 42 is formed, through which the windings of coil 43 run. The electro-magnetic drive mechanism, herein disclosed, is properly insulated and sealed in order to protect it from the ultrasound-transmitting liquid which surround it.

The required dynamically changeable magnetic field is generated by the described electro-magnet. The armature is moved according to the respective polarity to perform one swivel motion during the changing field. At the same time one of transducer elements 21 or 31 can be activated for ultrasound radiation or receiving.

Signal processing units as well as the electrical wiring are not shown in the enclosed figures. However, as can be seen, there is enough space in guiding element 4, as denoted by reference numeral 50, to hold such configurations. Therefore, applicator housing 1 as such can be of extremely compact design.

The structural configuration of the electro-magnet with double yoke 40 and coil 43 can be seen in the cross-section illustrated in FIG. 3. The detailed illustration of ultrasound transducer head 20 as an armature with a permanent magnet includes the following: Supporting element 27 is arranged on axis of rotation 26. Permanent magnet layer 23 is located on supporting element 27. Armature element 22 has been adapted to the form of the pole shoe of double yoke 40 and is located in a shaft-like recess of the actual synthetic housing. Metal flag 28 has been provided for control purposes at the side of the armature element. As a result, a variable capacitor is formed, which can be used for determining the position of the swivelling armature and for control purposes as well.

The armature and capacitative measuring elements are of identical design in the second ultrasound transducer head 30. The structure of the rotatable ultrasound transducer head with capacitative measuring elements are detailed in FIG. 4. Identification numbers for the swivel axis (axis of rotation) for the transducer elements and the permanent magnet layer were already provided above. In park position, metal flags 28 and 29 are positioned opposite one another to form a capacitor. By rotating the ultrasound transducer head, the effective surface is changed, whereby each position of the transducer element can be determined.

As can be seen in detail from the description of the embodiments and figures, an electro-magnetic drive is especially suitable for a compact device design according to the present invention. However, an applicator housing with two ultrasound transducer heads arranged opposite one another at the distal end, can also include a mechanical drive, while maintaining the advantages with respect to application and easy handling. Consequently, an applicator with mechanical drive is also part of the present invention.

There has thus been shown and described novel apparatus for ultrasound scanning which fulfills all the objects and advantages sought therefor. Many changes, modifications, variations and other uses and applications of the subject invention will, however, become apparent to those skilled in the art after considering this specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. An ultrasound device for sector scanning an object, said device having an ultrasound transmitting/receiving system which comprises in combination:

(a) an applicator housing having an elongated shape with opposed ends thereof each being enclosed by a respective spherical calotte-shaped cap, said cap containing a coupling fluid for coupling ultrasonic waves;

(b) first and second ultrasound transducer heads, each transducer head operating on a different frequency from the other and having at least one transducer element, the heads being rotatably mounted within said opposed ends of said applicator housing and being mounted such that their respective transducer elements radiate ultrasound away from each other; and (c) single drive means for moving said first and second ultrasound transducer head to produce a scanning type motion for each of them in a manner that the effects of undesirable mechanical inertial forces generated within either one of the rotating transducer heads are nullified by opposed inertial forces generated within the other one of the rotating ultrasound transducer heads.

2. The ultrasound device according to claim 1, further comprising a guiding element for guiding means and pivotably supporting said applicator housing, said guiding element being operative to allow said housing to be swivelled or rotated so that one or the other of said first and second transducer heads can be positioned to face said patient under examination.

3. The ultrasound device according to claim 2, further comprising signal processing means ultrasound transducer heads and wherein said guiding element includes a bore therethrough to define an enclosure, said signal processing means being arranged within said enclosure of said guiding element to reduce space requirements within said applicator housing.

4. The ultrasound device as recited in claim 1, wherein said single drive means comprises an electro-magnetic drive mechanism which includes a double yoke having pole shoes of opposite polarity and respective coil winding, and wherein said first and second ultrasound transducer heads are arranged as swivelling armatures between their respective pole shoes.

5. The ultrasound device as recited in claim 4, wherein the sides of said first and second ultrasound transducer heads facing said pole shoes are covered with a permanent magnet layer.

6. The device of claim 5, wherein said permanent magnet is comprised of rare earths.

7. The device of claim 1, wherein said single drive means further comprise a capacitive signal means for determining the angular positions of said first and second ultrasound transducer heads.

8. The device as in claim 7, wherein said capacitive signal means comprises a variable capacitor which comprises first and second metal flags attached respectively to each of said first and second swivelling ultrasound transducer heads so that the overlapping of said first and second metal flag with stationary metal flags positioned opposite thereto allows a determination as well as control of the angular position of said first and second ultrasound transducer elements.

9. The device as recited in claim 5, wherein said double yoke comprises a layer of transformer stampings punched out to define the shape of said double yoke.

10. The ultrasound device according to claim 5, wherein said electro-magnetic drive mechanism is properly insulated and sealed to be protected from said coupling fluid.

* * * * *